United States Patent
Xu et al.

(10) Patent No.: US 6,299,910 B1
(45) Date of Patent: Oct. 9, 2001

(54) **METHODS FOR IDENTIFICATION, PURIFICATION, AND MANUFACTURING OF THE ACTIVE CONSTITUENT IN *SALVIA-MILTIORRHIZA* (DANSHENG) AND THE APPLICATION OF THIS PRODUCT IN ENHANCING CARDIOVASCULAR FUNCTIONS**

(75) Inventors: Yaming Xu, Shanghai; Lijiang Xuan, Shanghai; Zhitian Li, Shanghai; Yunlong Gu, Shanghai, all of (CN); Steve Lee, Missoula, MT (US)

(73) Assignee: Techical Sourcing International, Inc., Missoula, MT (US)

( * ) Notice: Subject to any disclaimer, the term of this patent is extended or adjusted under 35 U.S.C. 154(b) by 0 days.

(21) Appl. No.: 09/543,854

(22) Filed: Apr. 5, 2000

Related U.S. Application Data

(60) Provisional application No. 60/129,516, filed on Apr. 7, 1999.

(51) Int. Cl.[7] ................................................. A61K 35/78
(52) U.S. Cl. ............................................. 424/746; 424/725
(58) Field of Search ................................ 424/195.1, 746, 424/725

(56) References Cited

U.S. PATENT DOCUMENTS 4,999,376 * 3/1991 Liu .
5,358,962 * 10/1994 Oura et al. .

OTHER PUBLICATIONS

Tanaka, Takashi et al.; Magnesium and Ammonium–Potassium Lithospermates B . . . Chem Pharm Bull vol. 37 No. 2 340–344 (1989).

Lian–Niang, Li Lian et al.;Salvianoclic aCID a nEW dEPOSIDE FROM rOOTS OF sALVIA MILTIORRHIZA, Planta Medica 1984 p 227–228.

YOKOZAWA, TAKAKO et al; RENAL RESPONSES TO MAGNESIUM LITHOSPERMATE B IN RATS WITH ADENINE–INDUCED RENAL FAILURE, Phytotherapy Research vol. 7. 235–239 (1993).

* cited by examiner

*Primary Examiner*—Francisco Prats
*Assistant Examiner*—Susan D. Coe
(74) *Attorney, Agent, or Firm*—Daniel R. Gropper, PC

(57) ABSTRACT

A method has been developed to extract and purify the chemical constituents in the traditional medicinal plant Salvia miltiorrhiza by an alcohol based method.

20 Claims, No Drawings

METHODS FOR IDENTIFICATION, PURIFICATION, AND MANUFACTURING OF THE ACTIVE CONSTITUENT IN *SALVIA-MILTIORRHIZA* (DANSHENG) AND THE APPLICATION OF THIS PRODUCT IN ENHANCING CARDIOVASCULAR FUNCTIONS

CROSS REFERENCE TO RELATED PATENT APPLICATION

This application is a continuation-in-part of provisional patent application Ser. No. 60/129,516 filed on Apr. 7, 1999.

FIELD OF THE INVENTION

This invention relates to methods for the water extraction and purification of Dansheng's active constituents; methods to identify a marker compound as well as an active compound in Dansheng; methods to qualitatively set up quality standards for Dansheng; and methods to eliminate toxic substances, such as Protocatechualdehyde, from the Dansheng extract.

BACKGROUND OF THE INVENTION

Dansheng, also known by its botanical name Salvia miltiorrhiza, belongs to the Labiatae family. The Dansheng herb is indigenous to the mountainous southern and central parts of China. Outwardly, the root is red. Internally, it is purplish when fresh. It is commonly sold in short, shriveled pieces of bright, brick-red color.

The Dansheng root is one of the traditional remedies for the five elements which are thought to correspond to five specific colors: yellow, white, black, purple, and red, which in turn are thought to correlate with the five principal visceral organs—spleen, lungs, kidneys, liver, and heart. Dansheng particularly belongs to the heart, and its red color traditionally suggests the blood and the circulation system.

Dansheng has been recommended for all blood difficulties including circulation, hemorrhages, menstrual disorders, and many heart disorders. In the thousands of years following its first appearance in old Chinese pharmacopoeia, the herb became one of the most significant remedies in Chinese folk medicine.

The chemical constituents of Dansheng can be divided into two categories: water-soluble and fat soluble. Due to limitations in chemical techniques, the herbal extract products manufactured up until recent years were confined primarily to fat-soluble compounds such as Tanshenone and its diperpenoid derivatives. These fat-soluble compounds were proven, to a limited degree, to be beneficial in treating physiological activities.

In 1980, Chen et al. began investigating some water-extracted components: Protocatechualdehydes, Danshensu (3',4 phenyllatic Acid), and the Salvianolic Acids A and B. These preliminary water-soluble chemicals were found to increase animal endurance capacity under hypoxia conditions.

There have been many articles published about the beneficial affects of Dansheng. Some of these include:

Nishioka I. et al., Magnesium and Amonium-Potassium Lithospermates B, the Active Principles Having a Uremia-Preventive Effect from Salvia miltiorrhiza, *Chem. Pharm. Bulletin* 37(2) 340–344(1989);

Yokozawa T. et al., Renal Response to Magnesium Lithospermate B in Rats with Adenine-induced Renal Failure, *Phytotherany Research*, Vol. 7. 235–239(1993);

Chen C. et al., Chemical Investigation on water soluble components of Salvia miltiorrhiza, *Phytotherapy Research*, Vol. 16, No. 9:536–538 (1981); and, Li L-N et al., Salvianolic Acid A, a New Depside from Roots of Slvia miltiorrhiza, *Planta Medica*, 227–228 (1994).

SUMMARY OF THE INVENTION

A feature of this invention is a method for the water extraction and purification of Dansheng's active constituents.

Another feature of this invention is a method to identify a marker compound as well as an active compound in Dansheng.

Another feature of this invention is a method to qualitatively set up quality standards for Dansheng.

Another feature of this invention is a method to eliminate toxic substances, such as Protocatechualdehyde, from the Dansheng extract.

Another feature of this invention is a method to extract active Magnesium Salvianolate compounds from Dansheng without creating additional unwanted polysaccharides, proteins and resins as are commonly created during the traditional water extract-alcohol precipitation.

DETAILED DESCRIPTION OF THE PREFERRED EMBODIMENTS

The active ingredients in Dansheng may be efficiently obtained by means of water extraction and separation by the following method.

Dansheng herb is chopped into pieces about 3 cm in length and are placed in a stainless steel extracting tank.

The chopped Dansheng is placed in boiling water at a temperature of about 100° C. at normal pressure. The mixture is boiled until the water is light brown to form a liquid form of extract of the Dansheng.

The extraction with boiling water should be performed two to three times. The first bath should be approximately 5 parts water to 1 part herb. Thus, 100 kg of material would require 500 liters of water in the first extraction. The second extraction should use 300 liters of water on the remaining product. The final extraction should use 250 liters on the remaining product.

Each extraction cycle with boiling water lasts for approximately two hours where the product in each cycle is boiled down to a concentration and then is siphoned off to an external vessel.

The extract is dried to ¼ volume at less than 50° C. using vacuum-aided concentration.

The combined extract is centrifuged until the product is concentrated into about 250 liters.

The centrifuge dried and separated filtrate is then passed through a resin for further column separation. Resins with properties similar to Sephadex LH-20, TSK gel Toyopearl 40F, MCI gel CHP 20p, and Cosmosil, Amberlite XAD or similar type of resin like No.:1300-1. Such resins are manufactured by Young Zhou Pharmaceutical Company. A 300 liter column of resin may be used for this separation.

The optimal amount of resin is about three parts resin to one part herb.

The impurities in the resin column are flushed with 600 liters of 95% alcohol solution, then with 800 liters of water.

The compound is washed with water and is flushed with 600 liters of a 50–60% alcohol solution, preferably ethanol, before being concentrated into final powder product. The optimal amount of alcohol solution is about 6–7 times the amount of the crude product.

Then about 90 liters anhydrous ethanol are added into the concentrate while stirring constantly. This second filtrate is again centrifuged and again vacuum dried into 2.5–3 kg brown Dansheng Salvianolate Salt Powder at less than 50° C. under a vacuum for 4–8hours.

This should yield 2–3 kg of Dansheng Salvianolate Salt Powder from 100 kg Dansheng.

Eight compounds are separated from the Dansheng using this water based separation process.

They are:

(1) Potassium 3' 4-dihydroxyphenyllactate;
(2) Sodium Rosmarinate;
(3) Dipotassium Lithospermate;
(4) Magnesium Lithospermate;
(5) Dipotassium Salvianolate B;
(6) Magnesium Salvianolate B;
(7) Magnesium Salvianolate G; and,
(8) Magnesium Isosalvianolate B.

The water extraction technique results in the recovery of the highest possible quantity of Magnesium Salvianolate B at 60% concentration, the most biologically effective compound recovered from the Dansheng.

Physioloaical Effects of the Eight Compounds Extracted from Dansheng

This process yields a minute amount of Magnesium Salvianolate G and accordingly the physiological effect of this compound is difficult to evaluate.

The other seven compounds are evaluated based on: [1] Their anti-oxidant activity, [2] Anti-platelet aggregation, and [3] Endurance under hypoxia conditions.

Compounds 6 and 8 effectively extended rats life up to 78% Other compounds are comparatively lower in this category (see Tables III and V below).

Compound 6 has the highest potency platelet anti-aggregation. (see Tables II and VI below).

All eight compounds showed antioxidant activity for liver cell protection.

Table I: Effect of Dansheng Constituents on Liver Cell MDA (Molonyldialdehyde) Amount Induced by Carbon Tetrachloride All compounds are equally active in this category.

Symbol: − Non Effect, * Effective, ** Very Effective

As shown in Tables II and III, Magnesium Salvianolate B, compound 6, has the highest bioactivity level in these three categories; platelet anti-aggregation, life extension under hypoxia condition (lack of oxygen), anti-oxidation (liver cell protection).

Potassium 3' 4-dihydroxyphenyllactate, Compound 1 has the lowest bio-activity level.

MSV (Magnesium Salvianolate B) is the most potent among all the components in inhibition of platelet aggregation which leads to arteriosclerosis and other blood vessel thrombosis which lead to cardiovascular diseases.

Bioactivities of Dansheng's active ingredient Magnesium Salvianolate B (MSV) includes liver protection from toxic pollutants. A concentration of 0.5 micro mole/ml MSV decreases the secretion of MDA from liver cell and enhanced endurance under hypoxia conditions (78% life extension compared to without MSV, at 200 mg/kg dose) and platelet anti-aggregation(94% inhibition at the concentration of 900 mcg/ml in Table II).

TABLE II

The Platelet Anti-aggregation Effect of Magnesium Salvianolate B and Its Derivatives

| Compound | Concentration (mcg/ml) | Inhibition % |
|---|---|---|
| #6 | 450 | 74 |
|  | 900 | 94 |
| #6 Derivatives | 450 | 22 |
|  | 900 | 68 |
| Salvianolate | 450 | 20 |
|  | 900 | 94 |
| Salvianolic Acid | 450 | 0 |
|  | 900 | 23 |

These results were from in vitro evaluation.

TABLE III

The Platelet Anti-aggregation Effect of Magnesium Salvianolate B and Its Derivatives

| Compound | % Life Extension |
|---|---|
| #6 | 78 |
| #6 Derivatives | 28 |
| Salvianolate | 78 |
| Other | 14 |

These results were from in vitro evaluation at 200 mg/kg dose.

TABLE IV

I Effect of Dansheng Components on Red Blood Cell lysis by $H_2O_2$

| Compound # | Degree of Inhibition | Effect |
|---|---|---|
| 1 | 100% | ++ |
| 2 | 100% | ++ |
| 3 | 100% | ++ |
| 4 | 100% | ++ |
| 5 | 100% | ++ |
| 6 | 100% | ++ |
| 8 | 100% | ++ |

These compounds were prepared at 0.33 mg/ml.

The symbols: − not effective, + effective, ++ very effective

TABLE V

Effect of Dansheng Components on Rats under Hypoxia Condition

| Compound # | Life Expanded, Statistics | | Effect |
|---|---|---|---|
| 1 |  | p >0.05 | — |
| 2 | 42% | p <0.01 | ++ |
| 3 | 23% | p <0.05 | + |
| 4 | 45% | p <0.05 | + |
| 5 |  | p >0.05 | — |
| 6 | 65% | p <0.01 | ++ |
| 8 | 69% | p <0.01 | ++ |

These results were from in vitro, 100 mg/kg dose.

Symbols: − not effective, + effective, ++ very effective

TABLE VI

Effect of Dansheng Components on Platelet Anti-aggregation

| Compound # | Concentration(mcg/ml) | % Inhibition | Effect |
| --- | --- | --- | --- |
| 1 | 180 | 0 | — |
|   | 900 | 0 | — |
| 2 | 180 | 0 | — |
|   | 900 | 13 | — |
| 3 | 180 | 0 | — |
|   | 900 | 18 | — |
| 4 | 180 | 0 | — |
|   | 900 | 28 | — |
| 5 | 180 | 0 | — |
|   | 900 | 44 | + |
| 6 | 180 | 0 | — |
|   | 450 | 15 | — |
|   | 900 | 74 | + |
| 8 | 180 | 0 | — |
|   | 900 | 20 | — | in vitro study

Symbols: − not effective, + effective, ++ very effective

What I claim is:

1. A method for the water based extraction of the active ingredients of Dansheng comprising the steps of:
   a) chopping raw Dansheng into pieces about 3 cm in length to form chopped Dansheng;
   b) placing said chopped Dansheng in an extracting tank with water;
   c) boiling said chopped Dansheng in said water at about 100 degrees C at normal pressure until liquid Dansheng extract is formed;
   d) siphoning said liquid Dansheng extract into a second vessel;
   e) vacuum drying said liquid Dansheng extract to form vacuum concentrated Dansheng extract;
   f) separating solids from liquids from within said vacuum concentrated Dansheng extract by centrifuge;
   g) passing the liquid vacuum concentrated Dansheng extract resulting from step f through a resin column for further separation; and,
   h) flushing effluent from said resin column with alcohol to result in a Dansheng extract.

2. A method for the water based extraction of the active ingredients of Dansheng, as recited in claim 1, further comprising the step of concentrating said Dansheng extract into a powder form.

3. A method for the water based extraction of the active ingredients of Dansheng, as recited in claim 1, wherein said pieces of chopped Dansheng are no longer than 3 cm.

4. A method for the water based extraction of the active ingredients of Dansheng, as recited in claim 1, wherein said extracting tank is stainless steel.

5. A method for the water based extraction of the active ingredients of Dansheng, as recited in claim 1, wherein steps c–h are repeated at least once on said Dansheng.

6. A method for the water based extraction of the active ingredients of Dansheng, as recited in claim 1, wherein steps c–h are repeated at least twice on said Dansheng.

7. A method for the water based extraction of the active ingredients of Dansheng, as recited in claim 1, wherein the ratio of said Dansheng to said water in said extracting tank is initially at least 5 parts water to 1 part Dansheng.

8. A method for the water based extraction of the active ingredients of Dansheng, as recited in claim 5, wherein the ratio of said Dansheng to said water in said extracting tank is initially at least 3 parts water to 1 part Dansheng at the beginning of the first repetition of steps c–h.

9. A method for the water based extraction of the active ingredients of Dansheng, as recited in claim 6, wherein the ratio of said Dansheng to said water in said extracting tank is initially at least 2.5 parts water to 1 part Dansheng at the beginning of the second repetition of steps c–h.

10. A method for the water based extraction of the active ingredients of Dansheng, as recited in claim 1, wherein each cycle comprising steps c–h is for about a 2 hour duration.

11. A method for the water based extraction of the active ingredients of Dansheng, as recited in claim 1, wherein during step e said Dansheng extract is dried to about ¼ volume using vacuum aided concentration.

12. A method for the water based extraction of the active ingredients of Dansheng, as recited in claim 11, wherein said vacuum aided concentration takes place at about 50 degrees C.

13. A method for the water based extraction of the active ingredients of Dansheng, as recited in claim 1, wherein about a 300 liter column of resin is used for separation.

14. A method for the water based extraction of the active ingredients of Dansheng, as recited in claim 1, wherein an optimal amount of resin is about three parts resin to one part Dansheng extract.

15. A method for the water based extraction of the active ingredients of Dansheng, as recited in claim 1, wherein during step h said Dansheng extract is flushed with 600 liters of 50%–95% alcohol solution.

16. A method for the water based extraction of the active ingredients of Dansheng, as recited in claim 1, further comprising a step wherein said Dansheng extract at the end of each cycle comprising steps c–h is flushed with at least 800 liters of water.

17. A method for the water based extraction of the active ingredients of Dansheng, as recited in claim 1, further comprising the step of flushing said Densheng extract with 600 liters of a 50–60% alcohol solution.

18. A method for the water based extraction of the active ingredients of Dansheng, as recited in claim 17, wherein the optimal amount of alcohol solution is about 6–7 times the amount of the Dansheng extract.

19. A method for the water based extraction of the active ingredients of Dansheng, as recited in claim 1, wherein eight compounds are separated from the Dansheng including:
   (1) Potassium 3' 4-dihydroxyphenyllactate;
   (2) Sodium Rosmarinate;
   (3) Dipotassium Lithospermate;
   (4) Magnesium Lithospermate;
   (5) Dipotassium Salvianolate B;
   (6) Magnesium Salvianolate B;
   (7) Magnesium Salvianolate G; and,
   (8) Magnesium Isosalvianolate B.

20. A method for the water based extraction of the active ingredients of Dansheng, as recited in claim 1, wherein Magnesium Salvianolate B at 60% concentration is recovered from said Dansheng extract.

* * * * *